(12) United States Patent
Chen et al.

(10) Patent No.: US 9,572,847 B2
(45) Date of Patent: Feb. 21, 2017

(54) METHOD FOR TREATING A LUNG TUMOR IN A SUBJECT IN NEED THEREOF

(71) Applicant: DSG TECHNOLOGY, INC., Taipei (TW)

(72) Inventors: Wei-Cheng Chen, Taipei (TW); Mei-Chou Lai, Taipei (TW); Shorong-Shii Liou, Taipei (TW); I-Min Liu, Taipei (TW)

(73) Assignee: Kingland Property Corporation, Ltd., Taipei (TW)

( * ) Notice: Subject to any disclaimer, the term of this patent is extended or adjusted under 35 U.S.C. 154(b) by 484 days.

(21) Appl. No.: 14/139,126

(22) Filed: Dec. 23, 2013

(65) Prior Publication Data
US 2015/0174181 A1    Jun. 25, 2015

(51) Int. Cl.
| | | |
|---|---|---|
| *A61K 36/06* | (2006.01) | |
| *A61K 36/062* | (2006.01) | |
| *A61K 36/068* | (2006.01) | |
| *A61K 36/07* | (2006.01) | |
| *A61K 31/575* | (2006.01) | |
| *A61K 31/7076* | (2006.01) | |
| *A61K 38/44* | (2006.01) | |
| *A61K 9/00* | (2006.01) | |
| *A61K 9/14* | (2006.01) | |
| *A61K 9/19* | (2006.01) | |
| *A61K 31/00* | (2006.01) | |

(52) U.S. Cl.
CPC ............. *A61K 36/07* (2013.01); *A61K 9/0053* (2013.01); *A61K 9/14* (2013.01); *A61K 9/19* (2013.01); *A61K 31/00* (2013.01); *A61K 31/575* (2013.01); *A61K 31/7076* (2013.01); *A61K 36/068* (2013.01); *A61K 38/446* (2013.01); *A61K 2236/00* (2013.01)

(58) Field of Classification Search
CPC ...................................................... A61K 36/07
USPC ................................................... 424/195.15
See application file for complete search history.

(56) References Cited

U.S. PATENT DOCUMENTS

| | | | |
|---|---|---|---|
| 7,569,234 B2 | 8/2009 | Liu et al. | |
| 2006/0099222 A1* | 5/2006 | Hattori ............... | C07D 207/444 424/195.15 |
| 2007/0116787 A1* | 5/2007 | Yao ...................... | A61K 31/366 424/725 |
| 2009/0196885 A1* | 8/2009 | Yao ...................... | A61K 31/366 424/195.15 |
| 2012/0294897 A1* | 11/2012 | Fiorentino Gomez ................ | A61K 36/185 424/282.1 |
| 2013/0089627 A1* | 4/2013 | Huang .................. | A61K 31/22 424/649 |
| 2013/0122035 A1 | 5/2013 | Sheng | |
| 2014/0105928 A1* | 4/2014 | Stamets ................ | A61K 36/07 424/195.15 |
| 2014/0220150 A1* | 8/2014 | Stamets ................ | A01N 63/04 424/537 |

FOREIGN PATENT DOCUMENTS

| | | | |
|---|---|---|---|
| CN | 1406626 A | | 4/2003 |
| CN | 102283329 A | * | 12/2011 |
| CN | 103083364 A | * | 5/2013 |
| CN | 103251658 A | * | 8/2013 |
| CN | 104706682 A | * | 6/2015 |

OTHER PUBLICATIONS

Primordia Website document entitled "Antrodia cinnamomea". 2011. 4-pages.*
Patel et al. J. Pharmacognosy and Phytochemistry. 2013. vol. 2, No. 1, pp. 315-319.*
Qing-Guang Wu et al., "Study Progress in Resisting Tumour with Aweto," Guiding Journal of TCM, vol. 11, No. 6, Jun. 2005, pp. 80-82.
Wu et al., "Study of methanol extract of Antrdia camphorate in regulating apoptosis of lung cancer cells," Bulletin of Taiwan Society of Laboratory Medicine, vol. 27-2, Jun. 2012, pp. 71-78.

* cited by examiner

*Primary Examiner* — Chris R Tate
(74) *Attorney, Agent, or Firm* — Muncy, Geissler, Olds & Lowe, P.C.

(57) ABSTRACT

The invention discloses an herbal extract of treating lung tumor. The herbal extract comprises *Antrodia cinnamomea* and *Cordyceps militaris*, and the herbal extract is manufactured as following: mingling *Antrodia cinnamomea* and *Cordyceps militaris* with a weight ratio being between 1:5 and 5:1 to obtain a mixture; blending the mixture with a solvent with a weight-volume percentage being 50%, followed by extracting at 40-90° C. to obtain a herbal solution; and concentrating the herbal solution to obtain the herbal extract.

3 Claims, 9 Drawing Sheets

METHOD FOR TREATING A LUNG TUMOR IN A SUBJECT IN NEED THEREOF

BACKGROUND OF THE INVENTION

1. Field of the Invention

The present invention generally relates to an herbal extract and, more particularly, to an herbal extract for inhibiting lung tumor proliferation. The present invention further relates to a method of treating lung tumor.

2. Description of the Related Art

In Taiwan, tumor is the most common cause of death in men and women, and among tumor, lung tumor is the most serious disease. In Western medicine, conventional lung tumor treatment includes surgery, radiation therapy and chemotherapy. However, surgery is ineffective. Radiation therapy and chemotherapy unduly damage normal cells neighboring tumor tissues and consequently induce side effects. Moreover, after radiation therapy and chemotherapy, the risk of metastasis into nearby tissue or other parts of the body still exist.

In traditional Chinese medicine, *Antrodia cinnamomea*, belonging Fungi, grows only on inner rotten walls of hollow materials from an endemic *Cinnamomum kanehirai*. *Antrodia cinnamomea*. *Antrodia cinnamomea* contains abundant active ingredients, such as superoxide dismulase, steroids polysaccharides and triterpenoids with anti-tumor activities.

*Antrodia cinnamomea* belongs to herbs with cold property. Although a short-term administration of *Antrodia cinnamomea* has a significant effect on removing free radicals, a long-term administration may decrease the concentration of free radicals in human body, resulting in a cold constitution with reduced immunity. For patients undergoing radiation therapy or chemotherapy, administration of *Antrodia cinnamomea* can decrease side effects caused by radiation therapy or chemotherapy at the beginning. However, a long-term administration of high dose of *Antrodia cinnamomea* may cause immunity reduction, such as a increasing possibility of blood infection.

*Cordyceps militaris*, belonging to herbs with warm property, is rich in cordycepin, proteins, superoxide dismulase, amino acids and micronutrients. *Cordyceps militaris* is used to relieve asthma, suppress cough and reinforce kidney. Furthermore, cordycepin can suppress tumor proliferation by activating adenosine receptors A3 of mouse melanoma and lung tumor cells.

SUMMARY OF THE INVENTION

It is therefore the objective of this invention to provide an herbal extract as a medication for lung tumor, combining with the conventional lung tumor treatment in Western medicine, and thereby decreasing side effects caused by radiation therapy and chemotherapy.

It is another objective of this invention to provide an herbal extract, moderating side effects, such as the decrease of free radicals, due to long-term administration of *Antrodia cinnamomea*.

It is yet another objective of this invention to provide a method of treating lung tumor, with the herbal extract as an active ingredient, to inhibit lung tumor proliferation.

One embodiment of the invention discloses an herbal extract comprising *Antrodia cinnamomea* and *Cordyceps militaris*, wherein the herbal extract is manufactured as following: mingling *Antrodia cinnamomea* and *Cordyceps militaris* with a weight ratio between 1:5 and 5:1 to obtain a mixture; blending the mixture with a solvent in a weight-volume percentage of 50%, followed by extracting at 40-90° C. to obtain an herbal solution; and concentrating the herbal solution to obtain the herbal extract.

In a preferred form shown, the weight ratio of *Antrodia cinnamomea* and *Cordyceps militaris* is 5:1.

In a preferred form shown, the solvent is 95% ethanol.

In a preferred form shown, the extraction is performed by double boiling at 50° C.

In a preferred form shown, the extraction is for 8 hours.

The other embodiment of the invention discloses a method of treating lung tumor, by administering the herbal extract to a subject in need thereof to inhibit lung tumor proliferation.

In another preferred form shown, the herbal extract is orally administered to the subject in need thereof.

In another preferred form shown, the herbal extract has a dosage being 0.1 to 0.6 grams of the herbal extract per kilogram of the subject in need thereof.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

An herbal extract according to preferred teachings of the invention comprises: *Antrodia cinnamomea* and *Cordyceps militaris*. In the embodiment, natural fruit bodies of *Antrodia cinnamomea* obtained from *Cinnamomum kanehirai* are used due to a higher content of triterpenoids compared with mycelia of *Antrodia cinnamomea*. Moreover, fruit bodies of *Cordyceps militaris* are used because the fruit bodies of *Cordyceps militaris* contain higher contents of adenosine and cordycepin than mycelia of *Cordyceps militaris*.

Preferably, the herbal extract according to preferred teachings of the invention is manufactured, by mingling *Antrodia cinnamomea* and *Cordyceps militaris* in an adequate ratio to obtain a mixture, extracting the mixture by a solvent to obtain a herbal solution, and concentrating the herbal solution to obtain the herbal extract of the invention.

In detail, the mixture is obtained by mingling *Antrodia cinnamomea* and *Cordyceps militaris* in a weight ratio between 1:5 and 5:1, with a preferable weight ratio being 5:1. Preferably, *Antrodia cinnamomea* and *Cordyceps militaris* are smashed into particles able to pass through a standard #30 sieve before the minglement, thereby increasing efficiency of the minglement and the extraction followed by.

The mixture further blends with the solvent in a weight-volume percentage of 50%. That is, 1 liter of the solvent is used to blend with 500 grams of the mixture. 95% ethanol may be chose as the solvent. The mixture is than extracted by the 95% ethanol at 40-90° C. for 8 hours to obtain the herbal solution. Preferably, the extraction is performed by double boiling at 50° C. The extraction may be performed for several times to totally dissolve the active ingredients of *Antrodia cinnamomea* and *Cordyceps militaris* in 95% ethanol.

The concentrating process of the embodiment is vacuum filtrated by a No. 3 filter paper, vacuum concentrated to remove the solvent (more than half of the solvent used in the extraction), and followed by freeze-drying at −60° C. After the concentrating process, the herbal extract with water content smaller than 2% is obtained.

According to active ingredients such as cordycepin, polysaccharides and triterpenes, the herbal extract poses effects on inhibiting lung tumor proliferation.

In order to evaluate the herbal extract of the invention comprises cordycepin, polysaccharides and triterpenes, and to further verify the herbal extract of the invention poses ability of inhibition lung tumor proliferation, trials (A) to (C) are performed as following.

Trial (A): Contents of Active Ingredients

Referring to Table 1, 500 grams of the mixtures (with different amount of *Antrodia cinnamomea* and *Cordyceps militaris*) are used in trial (A). The mixtures blend with 1 liter of 95% ethanol and the extraction is performed by double boiling at 50° C. for 8 hours. The resulted product are further filtrated by a No. 3 filter paper, vacuum concentrated to remove 95% ethanol (more than half of 95% ethanol used in the extraction), followed by freeze-drying at −60° C. to obtain the herbal extracts of groups A1 to A7.

Following trials with the herbal extracts are carried on. The yield (%) shown in Table 1 is calculated as the following formula:

Yield(%)=(obtained amounts)/500×100%

TABLE 1

Herbal extracts used in trial (A) and extracting yields thereof

| | Amounts of mixtures (g) | | Herbal extract | |
| --- | --- | --- | --- | --- |
| Groups | Antrodia cinnamomea | Cordyceps militaris | Obtained amounts (g) | Yield (%) |
| A1 | 500 | 0 | 40.3 ± 1.8 | 8.06 ± 0.6 |
| A2 | 416.7 | 83.3 | 45.6 ± 1.3 | 9.12 ± 0.3 |
| A3 | 375 | 125 | 43.9 ± 0.9 | 8.78 ± 0.5 |
| A4 | 250 | 250 | 42.6 ± 1.4 | 8.52 ± 0.8 |
| A5 | 125 | 375 | 40.1 ± 1.0 | 8.02 ± 0.5 |
| A6 | 83.3 | 416.7 | 42.4 ± 0.9 | 8.41 ± 0.6 |
| A7 | 0 | 500 | 39.9 ± 1.2 | 7.98 ± 0.4 |

Moreover, 2 grams of the herbal extracts shown in Table 1 are ultrasonic vibrated with 5 mL of methanol for 15 minutes, followed by centrifugation at 3000 rpm for 10 minutes. 5 mL of supernatants are collected into new tubes, followed by heating with 100° C. water bath to dry.

For analyzing cordycepin, C18 (5 μm) 150 mm×4.6 mm column is used. A mobile phase is 40% methanol solution (mixed with water). A flow rate of the mobile phase is 1 mL/min. Absorbance of 260 nm is detected.

With reference to Table 2, group A7 with 100% *Cordyceps militaris* has a highest content of cordycepin being 8.25±0.29 ppm, while group A6 has an content being 6.57±0.24 ppm. In group A1 without *Cordyceps militaris*, cordycepin is in a not detected level.

TABLE 2

Contents of active ingredients of herbal extracts in trial (A)

| | Contents of active ingredients (ppm) | | |
| --- | --- | --- | --- |
| Groups | Cordycepin | Polysaccharides | Triterpenes |
| A1 | N.D. | 60.09 ± 1.56 | 32.45 ± 1.12 |
| A2 | 1.37 ± 0.15 | 61.33 ± 2.09 | 28.77 ± 1.08 |
| A3 | 2.06 ± 0.16 | 51.16 ± 1.24 | 26.15 ± 1.13 |
| A4 | 4.70 ± 0.19 | 15.92 ± 1.31 | 21.56 ± 1.19 |
| A5 | 5.52 ± 0.35 | 14.37 ± 14.38 | 24.67 ± 1.29 |
| A6 | 6.57 ± 0.24 | 14.38 ± 1.02 | 18.26 ± 1.23 |
| A7 | 8.25 ± 0.29 | 13.09 ± 1.37 | 19.16 ± 1.42 |

Next, for analyzing polysaccharides, a standard curve is prepared using different concentrations of galactose. The herb extract (1 mL) in Table 1 mixes with phenol solution (1 mL, 5%), and then subjected to a direct stream of concentrated sulfuric acid (5 mL). After cooling for 30 minutes, absorbance of 490 nm is measured using Hitachi U1800 spectrometer. Concentrations of polysaccharides are calculated according to the standard curve.

With reference to Table 2, group A2 has a highest content of polysaccharides being 61.33±2.09 ppm, while group A1 has an content being 60.09±1.56 ppm. In group A7 with 100% *Cordyceps militaris*, polysaccharides has a lowest content being 13.09±1.37 ppm.

Finally, for analyzing triterpenes, Purospher STAR (purchased from Merck) RP-18e (5 μm) 250 mm×4 mm column is used. A mobile phase is acetonitrile and 0.085% phosphoric acid mixed in a volumetric ratio of 47:53. A flow rate of the mobile phase is 1 mL/min. Absorbance of 254 nm is detected, as shown in FIGS. 1A to 1G With reference to Table 2, group A1 has a highest content of triterpenes with 100% *Antrodia cinnamomea* being 32.45±1.12 ppm, while group A2 has an content being 28.77±1.08 ppm. In group A6 has a lowest content being 18.26±1.23 ppm.

Furthermore, table 3 shows contents of several triterpenoids, such as antcin K, antcin C, zhankuic C, dehydrosulphurenic acid, zhankuic acid A and dehydroeburicoic acid. Also referring to FIGS. 1A, 1B, 1C and 1E, the herbal extract being groups A1, A2, A3 and A5 contain antcin K, antcin C, zhankuic C, dehydrosulphurenic acid, zhankuic acid A and dehydroeburicoic acid with the highest content of 68.78% (group A1).

TABLE 3

Contents of triterpenoids of herbal extracts in trial (A)

| | | Active ingredients | | | | |
|---|---|---|---|---|---|---|
| | | Antcin K | | Antcin C | | Zhankuic acid C |
| Peak | | 1a | 1b | 2a | 2b | 3a | 3b |
| Retention time (min) | | 8.70 | 9.18 | 30.94 | 33.11 | 34.82 | 36.20 |
| Ratios of Peak Area (%) | A1 | 9.99 ± 0.23 | 14.10 ± 0.26 | 6.32 ± 0.18 | 4.52 ± 0.09 | 7.37 ± 0.12 | 11.56 ± 0.16 |
| | A2 | 8.23 ± 0.09 | 12.52 ± 0.11 | 2.28 ± 0.13 | 0.50 ± 0.03 | 0.65 ± 0.16 | 1.50 ± 0.08 |
| | A3 | 0.83 ± 0.11 | 1.12 ± 0.08 | 0.08 ± 0.03 | 0.07 ± 0.02 | 1.42 ± 0.10 | 2.09 ± 0.06 |
| | A4 | N.D. | N.D. | N.D. | N.D. | N.D. | N.D. |
| | A5 | 1.40 ± 0.08 | 1.80 ± 0.12 | 0.20 ± 0.09 | 0.20 ± 0.07 | 0.91 ± 0.06 | 1.55 ± 0.13 |
| | A6 | N.D. | N.D. | N.D. | N.D. | N.D. | N.D. |
| | A7 | N.D. | N.D. | N.D. | N.D. | N.D. | N.D. |

| | | Active ingredients | | | |
|---|---|---|---|---|---|
| | | Dehydrosulphurenic acid | Zhankuic acid A | | Dehydroeburicoic acid | |
| Peak | | 4 | 5a | 5b | 6 | Total |
| Retention time (min) | | 52.81 | 61.05 | 61.70 | 95.31 | |
| Ratios of Peak Area (%) | A1 | 4.69 ± 0.21 | 4.09 ± 0.14 | 2.42 ± 0.09 | 3.71 ± 0.17 | 68.78 ± 0.25 |
| | A2 | 1.76 ± 0.12 | 1.58 ± 0.09 | 0.54 ± 0.07 | 8.03 ± 0.05 | 37.60 ± 0.22 |
| | A3 | 8.84 ± 0.12 | 0.94 ± 0.05 | 0.55 ± 0.04 | 12.09 ± 0.09 | 28.03 ± 0.16 |
| | A4 | N.D. | N.D. | N.D. | N.D. | N.D. |
| | A5 | 5.67 ± 0.05 | 0.72 ± 0.05 | 0.51 ± 0.03 | 6.47 ± 0.16 | 19.43 ± 0.20 |
| | A6 | N.D. | N.D. | N.D. | N.D. | N.D. |
| | A7 | N.D. | N.D. | N.D. | N.D. | N.D. |

Accordingly, the herbal extract of the invention is rich in cordycepin, polysaccharides and triterpenes.

Trial (B): In Vitro Pharmacological Study of the Herbal Extract of the Invention A549 (human lung tumor cell line) purchased from the Food Industry Research and Development Institute in Taiwan is used in trial (B). The A549 cells are cultured in medium (F-12K) containing 10% FBS (purchased from Biological Industries, Kibbutz beit haemek), 2 mmol/L $_L$-glutamine (purchased from HyClone, USA), 1× nonessential amino acids (purchased from HyClone, USA) and 100 U/mL penicillin. The A549 cells are incubated in an incubator with temperature of 37° C., $CO_2$ concentration of 5% and humidity of 95%. Medium used for culturing the A549 cells is renewed once in two days.

While subculturing, the A549 cells are centrifuged at 1000 rpm for 5 minutes to remove supernatants, followed by mixing with fresh medium. The A549 cells preferably have a concentration of $1\times10^5$ to $1\times10^6$ cells/mL in 10 cm culturing dishes.

The culturing dishes 80 to 90% of bottom areas covered by the A549 cells are used in trial (B). Discolored medium is removed, 8 mL of PBS solution is used to wash the A549 cells and Trypsin/EDTA is added into the culturing dishes for 1 to 3 minutes. After the A549 cells dissociate with walls of the culturing dishes by slightly vortexing, the A549 cells are resuspended with prewarmed medium. The A549 cells are collected into centrifuge tubes, followed by centrifugation at 1500 rpm for 10 minutes. Supernatants are removed and the A549 cells are resuspended in medium containing FBS. 20 μL of the A549 cells are collected, and 20 μL of trypan blue is added to the A549 cells for staining. The stained A549 cells are collected in cell counters, and numbers of the stained A549 cells are counted under microscope. Only the A549 cells with viability over 85% are suitable for the following experiments.

Concentrations of the A549 cells are adjusted to $1\times10^5$ cells/mL by medium containing FBS. 100 μL of the A549 cells with a concentration of $1\times10^4$ cells per are inoculated in a 96-well plate. The inoculated A549 cells are overnight cultured in an incubator with temperature of 37° C. and $CO_2$ concentration of 5%.

After culturing for 24 hours, the herbal extracts shown in Table 2 (in a concentration being 1, 0.5, 0.25 or 0.125 mg/mL) are added into each well of the 96-well plate. The A549 cells are overnight cultured in an incubator with temperature being 37° C. and $CO_2$ concentration being 5%.

TABLE 4 treatment used in trial (B)

| Groups | Treatment |
|---|---|
| B1 | F-12K |
| B2 | DMSO |
| B3 | Herbal extract (group A1) |
| B4 | Herbal extract (group A2) |
| B5 | Herbal extract (group A3) |
| B6 | Herbal extract (group A4) |
| B7 | Herbal extract (group A5) |
| B8 | Herbal extract (group A6) |
| B9 | Herbal extract (group A7) |

After culturing for 24 hours, medium is removed, and the A549 cells are washed by a PBS solution. 100 μL of CCK-8 containing-fresh medium is added into each well of the 96-well plate. The A549 cells react with CCK-8 for 2 hours in the incubator (37° C., 5% $CO_2$), followed by vortexing for 5 minutes. Absorbance of 450 nm of the tumor cells in each well is detected.

Figure 1A:
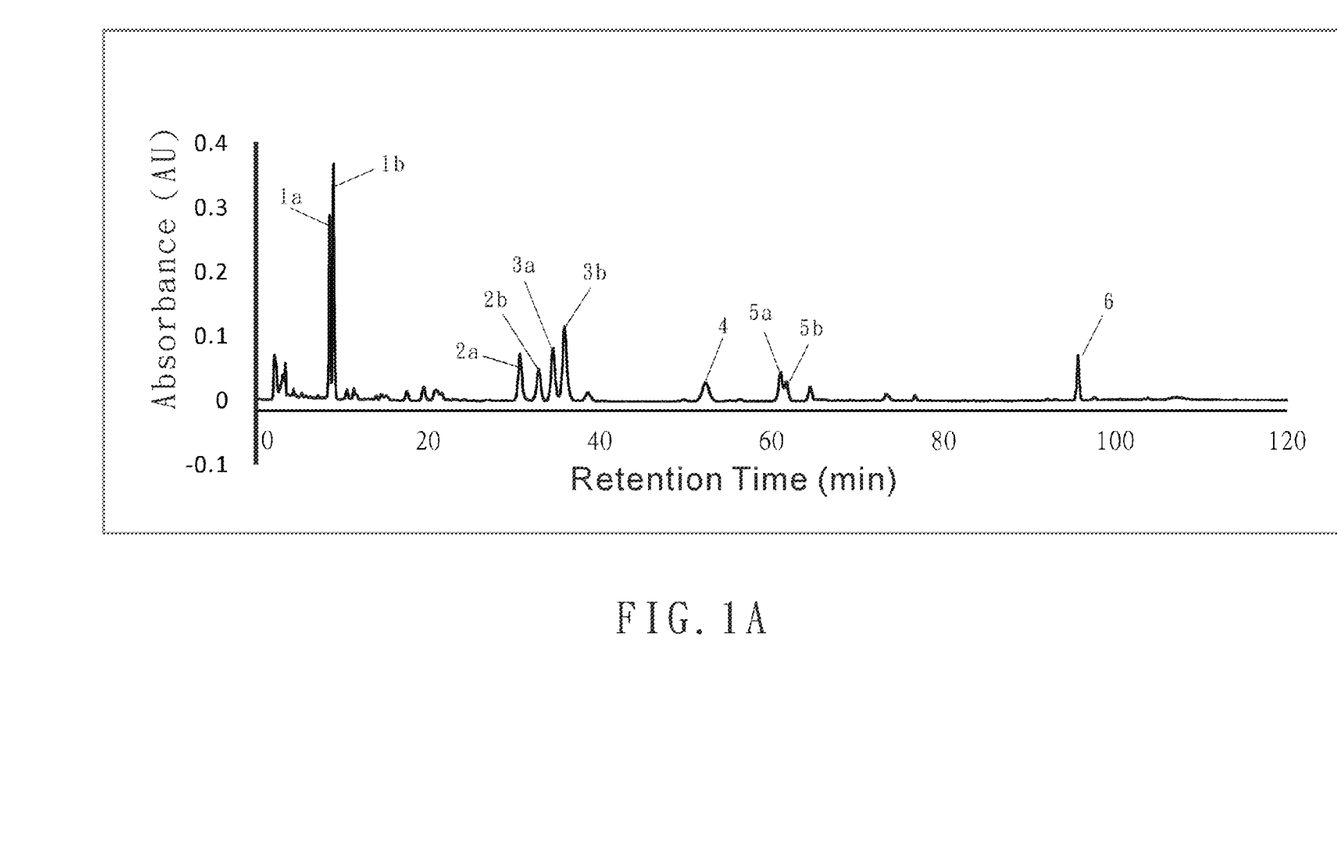
FIG. 1A depicts content of triterpenoids of group A1 using HPLC analysis.
Figure 1B:
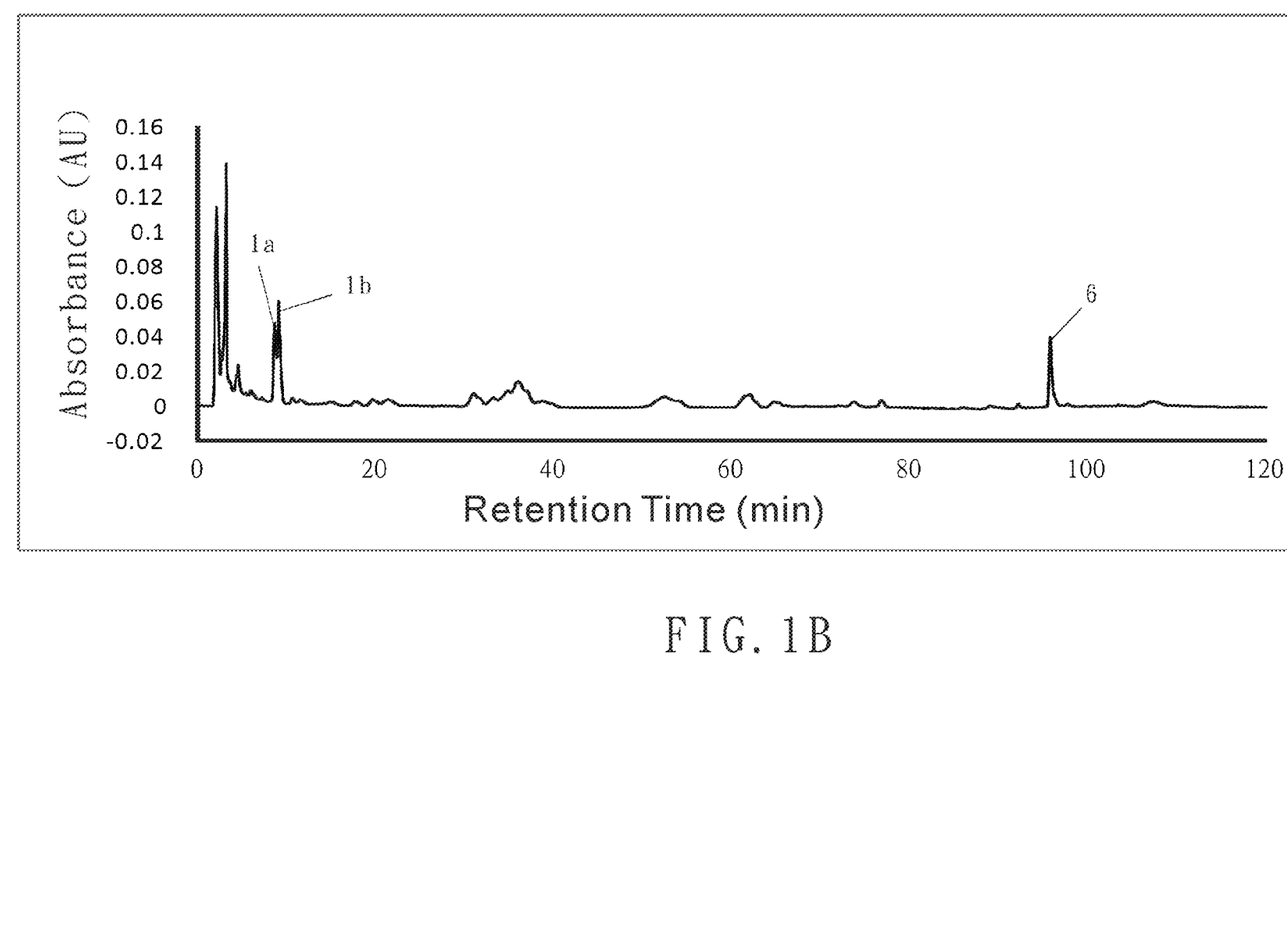
FIG. 1B depicts content of triterpenoids of group A2 using HPLC analysis.
Figure 1C:
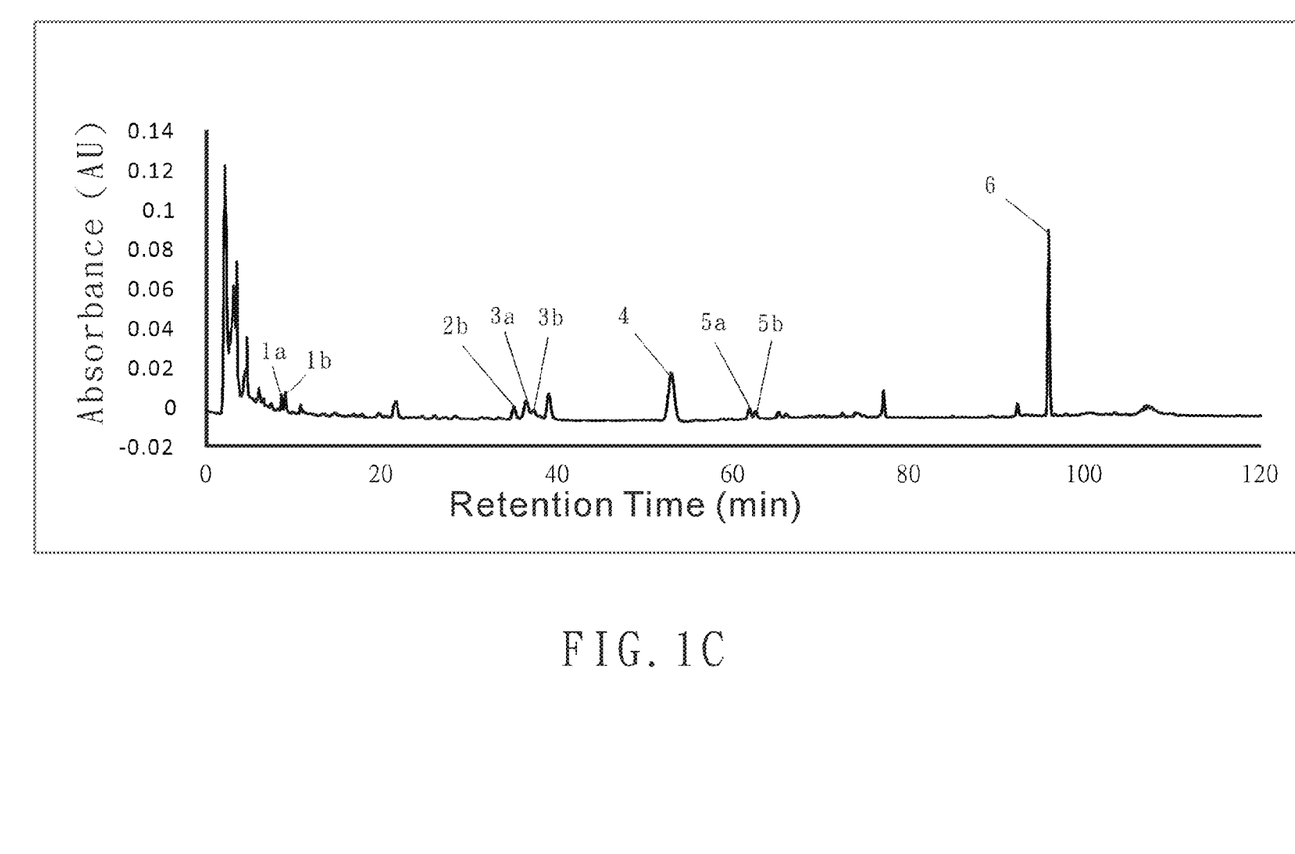
FIG. 1C depicts content of triterpenoids of group A3 using HPLC analysis.
Figure 1D:
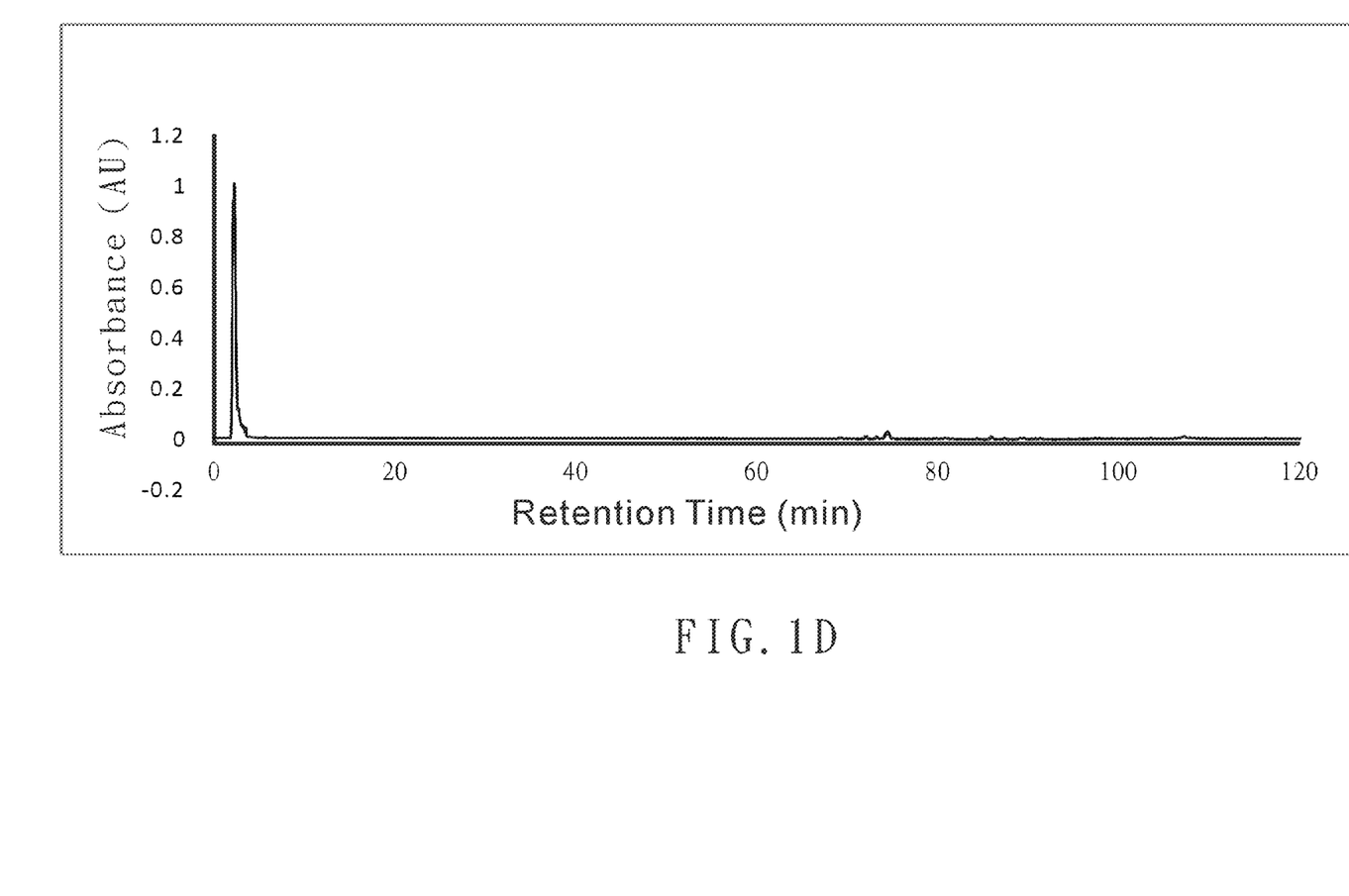
FIG. 1D depicts content of triterpenoids of group A4 using HPLC analysis.
Figure 1E:
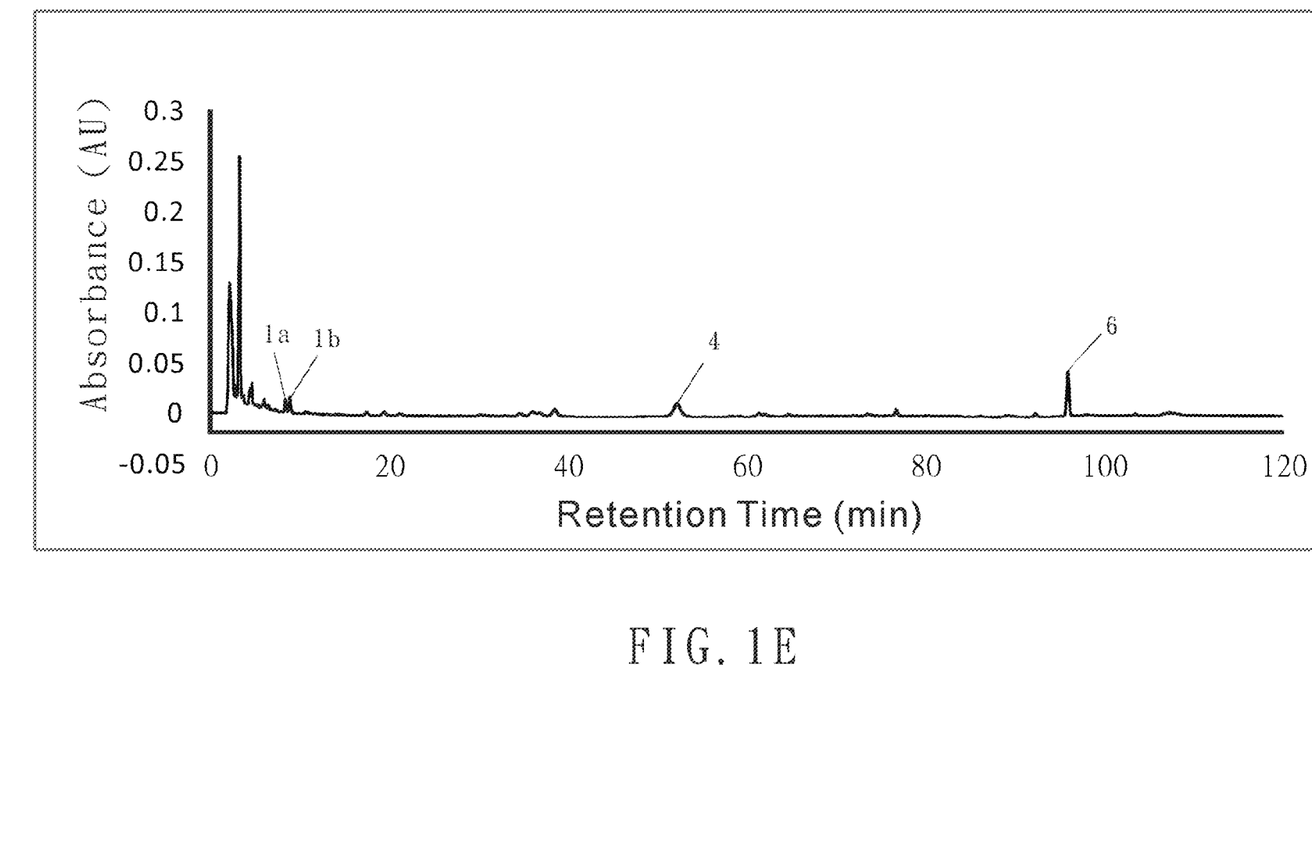
FIG. 1E depicts content of triterpenoids of group A5 using HPLC analysis.
Figure 1F:
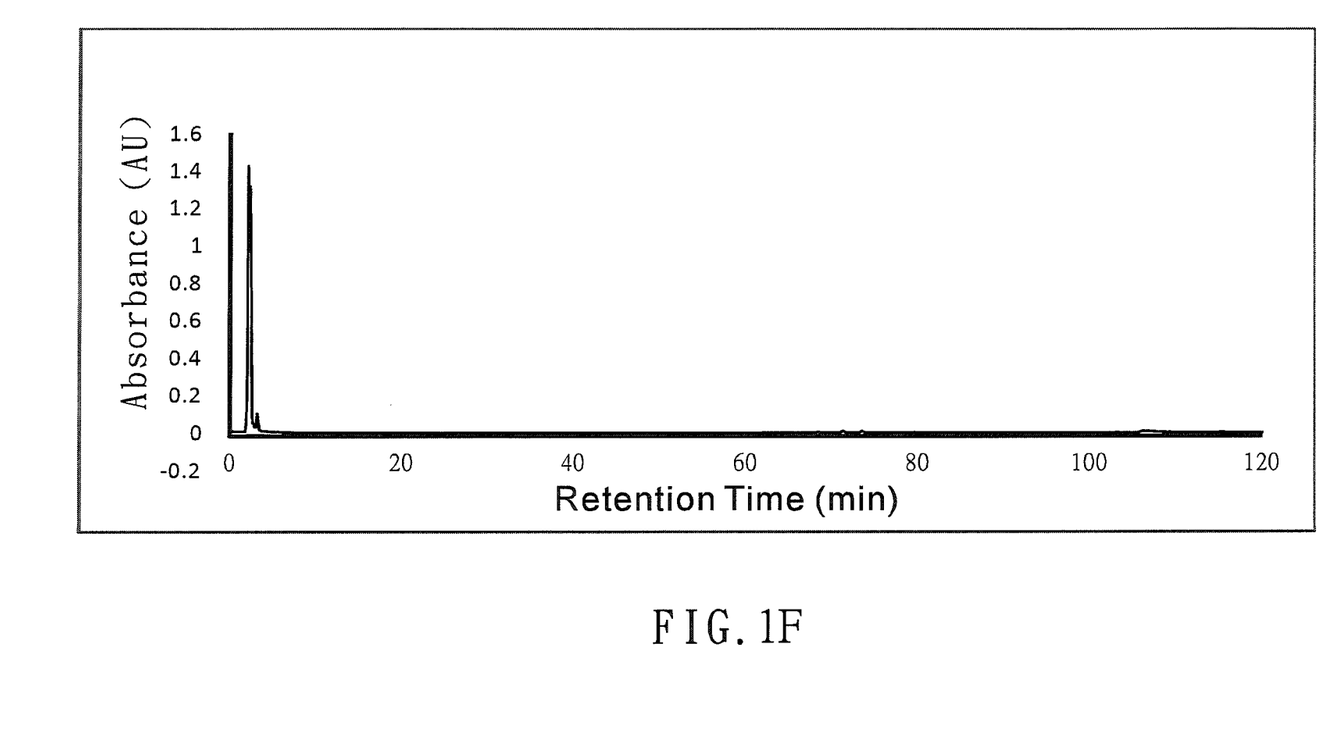
FIG. 1F depicts content of triterpenoids of group A6 using HPLC analysis.
Figure 1G:
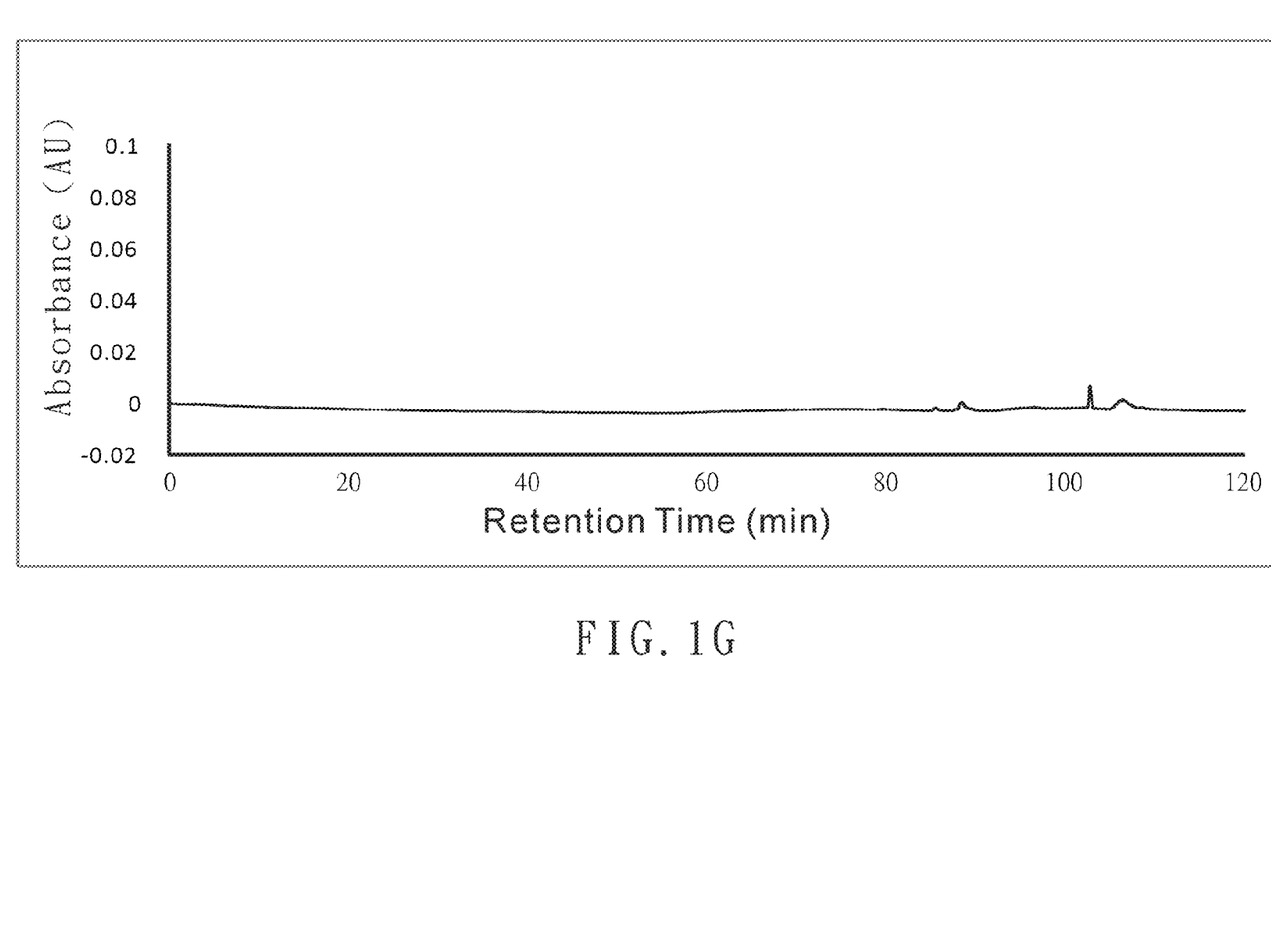
FIG. 1G depicts content of triterpenoids of group A7 using HPLC analysis.
Figure 2:
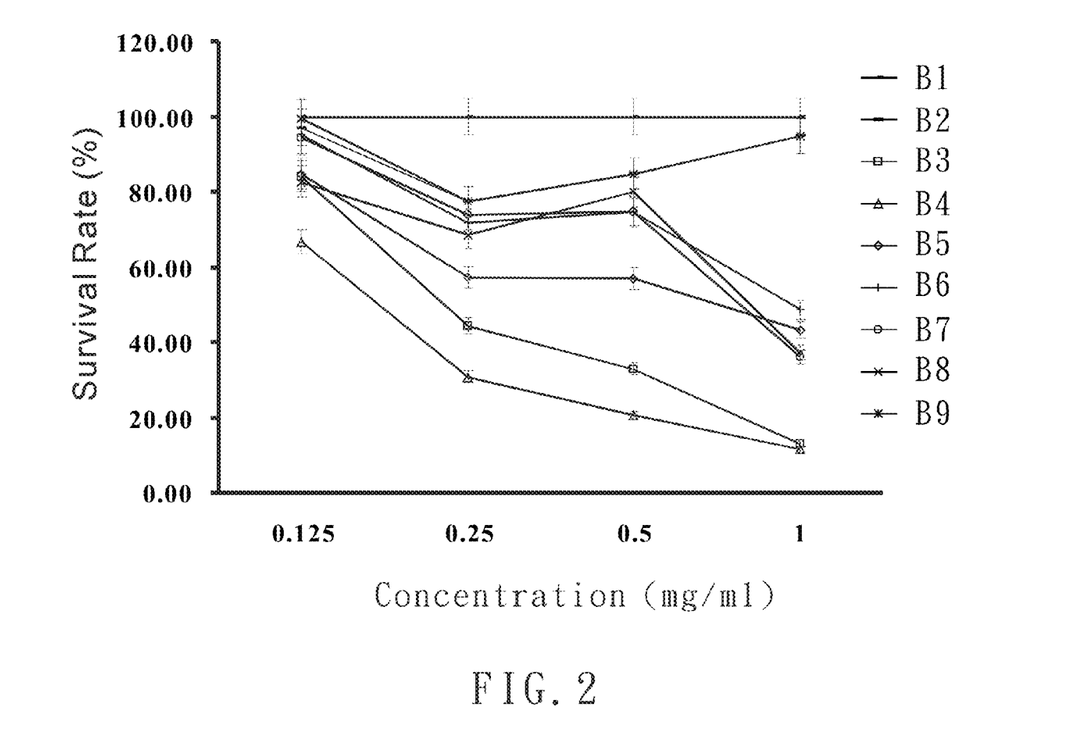
FIG. 2 depicts a line chart showing cell survival rates of groups B1 to B9.
Figure 3A:
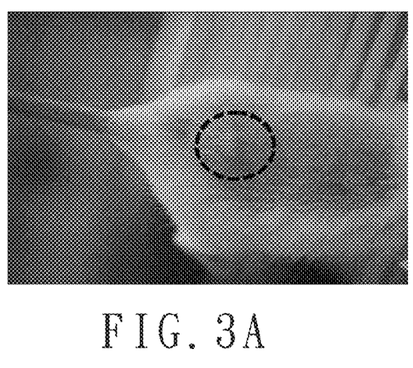
FIG. 3A depicts a photo showing appearance of tumor of group C1.
Figure 3B:
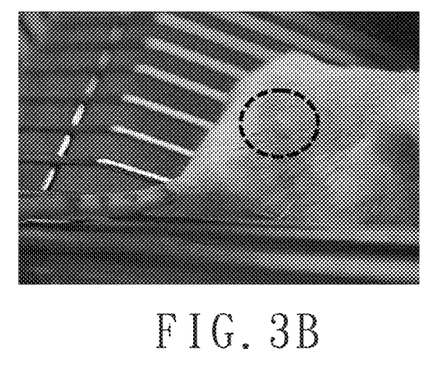
FIG. 3B depicts a photo showing appearance of tumor of group C2.
Figure 3C:
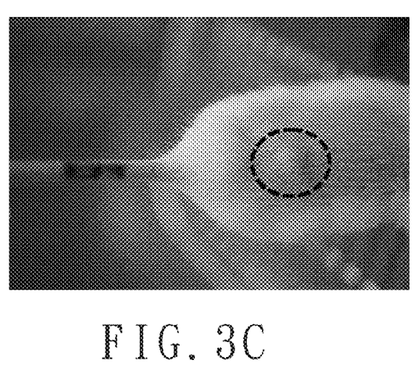
FIG. 3C depicts a photo showing appearance of tumor of group C3.
Figure 3D:
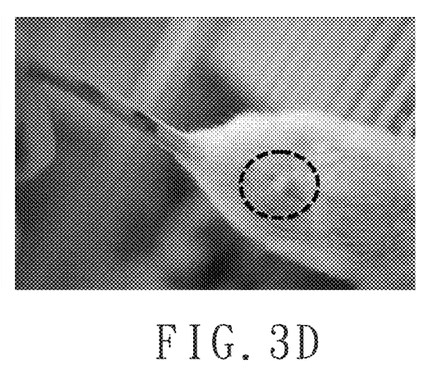
FIG. 3D depicts a photo showing appearance of tumor of group C4.

FIG. 2 depicts the line chart of survival rate of the A549 cells treated with the herbal extracts shown in Table 4. The survival rate is computed as followed:

Survival rate(%)=(Absorbance of a testing set/Absorbance of a control set)×100%

Referring to FIG. 2, compared to group B3 or B9, group B4 shows a lower survival rate. That is, the herbal extract according to preferred teachings of the present invention poses a better effect on inhibiting lung tumor cell proliferation.

Trial (C): In Vivo Pharmacological Study of the Herbal Extract of the Invention

Specific-pathogen free Balb/C male mice (8 week-old, weight 20 to 25 grams) purchased from the animal center of the national Cheng Kung University are used in trial (C). The mice are housed in an animal room with constant temperature of 25±1° C. where is kept on a 12-hours light and 12-hours dark cycle. The mice are housed and kept on free diet and water, which provided by the animal center of the national Cheng Kung University.

The A549 cells are diluted to a concentration of $5\times10^6$ cells/mL by a saline solution. The diluted A549 cells are inoculated to the mice via axillary subcutaneous injection.

Referring to Table 5, the herbal extract of group A2 is orally administered to the mice in a dosage of 0.1 grams per kilograms of the mice per day (group C2), 0.3 grams per kilograms of the mice per day (group C3) and 0.5 grams per kilograms of the mice per day (group C4). Group C1 is a control set without the herbal extract (orally fed with RO water in a dosage being 10 mL per kilograms of the mice per day). The mice are kept on free diet for 30 days. Tumor burden is monitored by X-ray once a week.

With respect to FIGS. 3A to 3D, compared with the group C1, oral administration of the herbal extract of the invention (groups C2 to C4) shows a significant decreasing on tumor size and tumor growth. Furthermore, the inhibition of tumor growth shows a positive correlation with the concentration of the herbal extract of the invention. Similar results are shown in Table 5 (*P<0.05).

TABLE 5

Tumor sizes of mice in trial (C)

| Groups | Treatment | Tumor size (mm³) | Tumor inhibition (%) |
|---|---|---|---|
| C1 | RO water (10 mL/kg/day) | 2.12 ± 0.47 | — |
| C2 | Herbal extract (0.1 g/kg/day) | 1.25 ± 0.31* | 40.04 ± 2.27 |
| C3 | Herbal extract (0.3 g/kg/day) | 1.17 ± 0.39* | 45.62 ± 2.73 |
| C4 | Herbal extract (0.5 g/kg/day) | 0.94 ± 0.25* | 55.73 ± 3.11 |

In addition, after sacrificing the mice, weights of thymus, spleen and tumor are measured. As shown in Table 6, in the aspect of body weight, thymus index (thymus size) and spleen index (spleen size), the treatment of the herbal extract of the invention (groups C2 to C4) shows no different from the group C1. That is, the herbal extract of the invention can specifically target the inoculated A549 cells.

TABLE 6

Physiological test of mice in trial (C)

| Groups | Treatment | Body weight (g) | Thymus (g) | Spleen (g) |
|---|---|---|---|---|
| C1 | RO water (10 mL/kg/day) | 25.7 ± 1.8 | 2.4 ± 0.5 | 19.8 ± 3.3 |
| C2 | Herbal extract (0.1 g/kg/day) | 26.3 ± 1.7 | 2.2 ± 0.6 | 18.2 ± 3.2 |
| C3 | Herbal extract (0.3 g/kg/day) | 25.7 ± 2.0 | 2.2 ± 0.7 | 17.7 ± 2.6 |
| C4 | Herbal extract (0.5 g/kg/day) | 25.9 ± 2.1 | 2.1 ± 0.5 | 17.4 ± 2.9 |

Moreover, renal and liver function is measured by analyzing blood with sysmex F-800 (Japan). Table 7 shows BUN (blood urea nitrogen) and creatinine with no significant difference among groups C1 to C4. However, as the amount of the herbal extract increases, the liver function index GOT (glutamic oxaloacetic transaminase) and GPT (glutamic pyruvic transaminase) decrease (*p<0.05). That is, the herbal extract of the invention pose protective effect on liver without inducing kidney injury.

TABLE 7

Renal and liver function test of mice in trial (C)

| Groups | Treatment | BUN (mg/dL) | Creatinine (mg/dL) | GOT (U/L) | GPT (U/L) |
|---|---|---|---|---|---|
| C1 | RO water (10 mL/kg/day) | 58.2 ± 6.1 | 0.67 ± 0.16 | 175.3 ± 3.5 | 10.7 ± 1.2 |
| C2 | Herbal extract (0.1 g/kg/day) | 54.5 ± 4.2* | 0.64 ± 0.10* | 165.7 ± 2.9 | 9.5 ± 0.9 |
| C3 | Herbal extract (0.3 g/kg/day) | 52.9 ± 4.9* | 0.63 ± 0.14* | 158.9 ± 2.8 | 8.7 ± 0.6 |
| C4 | Herbal extract (0.5 g/kg/day) | 51.2 ± 3.5* | 0.62 ± 0.16* | 152.7 ± 2.3 | 8.2 ± 0.4 |

Accordingly, the herbal extract of the invention is rich in polysaccharides, cordycepin and triterpenes, thereby posing effect on decreasing survival rate of lung tumor cells, inhibiting lung tumor proliferation.

The herbal extract of the invention can be combined with the conventional lung tumor treatment in Western medicine, so that decreases radiation dose or prevents from high-dose chemotherapy in the conventional lung tumor treatment, and further lower the side effects caused by the conventional lung tumor treatment.

The herbal extract of the invention, compared to the single extracts of *Antrodia cinnamomea*, shows a preferably inhibitory effect on lung tumor. In accordance with combination with *Cordyceps militaris*, the side effects caused by long-term administration of *Antrodia cinnamomea* can be effectively reduced.

Moreover, by administering the herbal extract of the invention containing abundant active ingredients such as polysaccharides, cordycepin and triterpenes, the method of treating lung tumor can effectively induce cytotoxicity and apoptosis in lung tumor, thereby preventing tumor from proliferation and metastasis.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating a lung tumor in a subject in need thereof comprising administering to said subject composition containing an effective amount of an extract, wherein the composition is prepared as follows:
   mixing *Antrodia cinnamomea* and *Cordyceps militaris* at a weight ratio of 5:1 to obtain a mixture;
   blending the mixture with a solvent at a weight-volume percentage of 50%, followed by extracting the blended mixture at 40-90° C. to obtain a solution; and
   concentrating the solution to obtain the extract.

2. The method of treating lung tumor as claimed in claim 1, wherein the composition is orally administered to said subject.

3. The method of treating lung tumor as claimed in claim 1, wherein the composition is administered as a dosage, said dosage containing from 0.1 to 0.6 grams of the extract per kilogram of said subject.

* * * * *